United States Patent
Joanny

(10) Patent No.: US 8,529,950 B2
(45) Date of Patent: *Sep. 10, 2013

(54) MAGNESIUM SYSTEM AND USE THEREOF IN THE COSMETICS INDUSTRY

(76) Inventor: Fabienne Joanny, Paris (FR)

(*) Notice: Subject to any disclaimer, the term of this patent is extended or adjusted under 35 U.S.C. 154(b) by 123 days.

This patent is subject to a terminal disclaimer.

(21) Appl. No.: 12/993,683

(22) PCT Filed: May 20, 2009

(86) PCT No.: PCT/FR2009/000586
§ 371 (c)(1),
(2), (4) Date: Nov. 19, 2010

(87) PCT Pub. No.: WO2009/150324
PCT Pub. Date: Dec. 17, 2009

(65) Prior Publication Data
US 2011/0097400 A1 Apr. 28, 2011

(30) Foreign Application Priority Data
May 20, 2008 (FR) .................................. 08 02702
Jul. 30, 2008 (FR) .................................. 08 04349

(51) Int. Cl.
*A61K 9/28* (2006.01)
*A61K 33/06* (2006.01)

(52) U.S. Cl.
USPC .......................................... 424/472; 424/682

(58) Field of Classification Search
USPC ................................................ 424/472, 682
See application file for complete search history.

(56) References Cited

U.S. PATENT DOCUMENTS

| | | | |
|---|---|---|---|
| 4,810,496 A * | 3/1989 | Jensen | 424/646 |
| 5,068,112 A | 11/1991 | Samejima et al. | |
| 5,135,850 A | 8/1992 | Prost | |
| 5,849,338 A | 12/1998 | Richardson et al. | |
| 5,898,037 A * | 4/1999 | Marx | 424/49 |
| 5,976,568 A | 11/1999 | Riley | |
| 6,887,492 B2 | 5/2005 | Kay et al. | |
| 2004/0156896 A1 | 8/2004 | Dixit et al. | |
| 2005/0220865 A1 | 10/2005 | Koleng et al. | |
| 2005/0266082 A1 | 12/2005 | Patel et al. | |
| 2006/0217385 A1 | 9/2006 | Edwards et al. | |
| 2006/0257483 A1 * | 11/2006 | Yang et al. | 424/471 |
| 2008/0031904 A1 * | 2/2008 | Menvielle-Bourg-Joanny | 424/401 |
| 2011/0091548 A1 | 4/2011 | Joanny | |

FOREIGN PATENT DOCUMENTS

| | | |
|---|---|---|
| EP | 0542979 | 12/1992 |
| FR | 2296426 | 7/1976 |
| FR | 2616068 | 12/1988 |
| GB | 1356097 | 6/1974 |
| WO | 0122943 A | 4/2001 |
| WO | 2004/105778 | 12/2004 |
| WO | 2005049053 | 6/2005 |
| WO | 2005091872 | 10/2005 |

OTHER PUBLICATIONS

Non-final Office Action dated Mar. 27, 2012 for U.S. Appl. No. 12/993,678, including lists of cited references and search strategy.
English translation (complete) of EP 0542979 (previously filed with IDS of Nov. 19, 2010).
Written Opinion from parent PCT application No. PCT/FR2009/000586.
Denda, M., "New strategies to improve skin barrier homeostatis", Advanced Drug Delivery Reviews, 54 Suppl.1, S123-S130, 2002.
Denda, M. et al., "Negative Electric Potential Induces Alteration of Ion Gradient and Lamellar Body Secretion in the Epidermis, and Accelerates Skin Barrier Recovery After Barrier Disruption", The Journal of Investigative Dermatology, vol. 118(1), pp. 65-72, 2002.
Roth, P. et al., 'Intestinal Absorption of Magnesium in Man', International Journal of Applied Radiation and Isotopes, vol. 30, pp. 523-526, 1979.
Berthelot, A. et al., 'Le Magnésium' pp. 27-30, John Libbey Eurotext editor (collection Pathology Science Formation), Dec. 2004 (English abstract attached).
Vippagunta et al, Advanced Drug Reviews, vol. 48, Abstract 2001.
Office Action dated Oct. 28, 2008 for U.S. Appl. No. 11/286,192, including lists of references.
Seelig, Journal of the American College of Nutrition, vol. 13, No. 5, Abstract, 1994.
Walker et al., Phytotherapy, vol. 16, pp. 48-54, 2002.
Galinksy et al, "Basic Pharmacokinetics and Pharmacodynamics" in Remington: The Science and Practice of Pharmacy (Baltimore, Lippencott Williams & Wilkins 2006), p. 1171.
Morissette et al, Advanced Drug Delivery Reviews, vol. 56, pp. 275-300, 2004.
International Search Report for PCT/FR2009/000586.
International Search Report for PCT/FR2009/000585.

* cited by examiner

*Primary Examiner* — Blessing Fubara
*Assistant Examiner* — Jennifer Berrios
(74) *Attorney, Agent, or Firm* — J-Tek Law PLLC; Jeffrey D. Tekanic

(57) ABSTRACT

A magnesium-based system suitable for use in skincare comprises (a) a first magnesium source in the form of a progressive-release oral tablet exhibiting in vitro, after 2h in 0.1N HCl medium, a rate of dissolution ($\delta$) of the magnesium contained therein of less than or equal to 60% by weight relative to the total weight of the Mg provided by the first magnesium source, and (b) a second magnesium source in a topical preparation. A method for treating skin for stress, fatigue or skin barrier deficiencies, as well as for stratum corneum hydration, includes orally and topically administering magnesium sources (a) and (b), respectively.

21 Claims, No Drawings

MAGNESIUM SYSTEM AND USE THEREOF IN THE COSMETICS INDUSTRY

CROSS-REFERENCE

This application is the US national stage of International Patent Application No. PCT/FR2009/000586 filed on May 20, 2009, which claims priority to French Patent Application No. 0804349 filed on Jul. 20, 2008 and French Patent Application No. 0802702 filed on May 20, 2008.

FIELD OF THE INVENTION

The present invention relates to a new magnesium-based system and to its use in cosmetology for the care and health of the skin and epidermal growths, especially with regard to stress for the skin, said system comprising an oral preparation containing a magnesium source, on the one hand, and a topical preparation likewise containing a magnesium source, on the other hand.

PRIOR ART

Within the body, magnesium in the ionic form $Mg^{2+}$ plays an important role in many biochemical reactions. It acts as an essential cofactor in all of the energy metabolism reactions involving adenosine triphosphate (ATP). Moreover, it is necessary for the interaction between actin and myosin, which is the basis of muscular contraction. It is likewise necessary for the synthesis of muscle fibers. In humans, after calcium and phosphorus, magnesium is the most abundant mineral in the body. Less than 1% of the total magnesium is found in the serum; approximately 60% is located in the mineral framework of the bone, 30% is located intracellularly in the muscles, and the remainder is located intracellularly in the other soft tissues.

At the cellular level, magnesium participates in the transmembrane ion exchange of cations. From the articles Denda, M., Adv. Drug Deliv. Rev., 2002 Nov., 1;54 Suppl. 1:S123-130 and Denda M. et al., J. Invest. Dermatol., 2002 January, 118(1):65-72, in particular, it is known that magnesium acts in close association with sodium, potassium, and calcium, with which it must remain in equilibrium within the body: the reason for this is that, to be healthy, the cell must be able to easily effect changes in ionic charge; the $Ca^{2+}$ cations and the $Mg^{2+}$ depolarize the cell upon entering it; the cations $Na^+$ and $K^+$ polarize the cell upon leaving it and thereby restore the return of the cell to its initial state.

Magnesium is a vital cofactor in the functioning of various ($Ca^{2+}$ and $Mg^{2+}$)-dependent membrane pumps. A deficiency in intracellular magnesium is likely to contribute to the blockage of the various reticular pumps, and hence to inhibit the outflow of calcium. Therefore, an increase in free intramyoplasmic calcium in the muscle fibers is responsible for spontaneous contractions, for exhaustion of ATP reserves, and, eventually, for tissue lesions.

It is known, in particular, that magnesium administered orally, having regard to its multipurpose effects, especially on the symptoms associated with the syndromes of overwork and fatigue, is widely used, alone or in combination, to respond to a variety of stress conditions:
stress associated with fatigue, with overwork or with intensive sport;
sleep disorders, insomnia, anxiety; and
stopping smoking, alcohol withdrawal.

Moreover, clinical studies have demonstrated the efficacy of magnesium salts in the treatment or prevention of a variety of pathological situations:
symptoms associated with menopause or with premenstrual syndrome (improved efficacy in combination with vitamin B6);
prevention of myocardial infarction, auxiliary treatment of arrhythmias and hypertension; and
other fields (prevention of diabetes and of osteoporosis, maintenance of muscular effort, enhancement of physical performance).

These pathological situations are encountered very frequently in cases of magnesium deficiency.

Moreover, it is known, from patent documents EP 0542979 B and WO 2004/105778 A in particular, that magnesium administered orally is useful in cosmetology, particularly for combating the manifestations of skin stress and of skin fatigue.

The publication WO 2005/049053 A proposed combating sexual dysfunction through the use of tablets, gel capsules, injectable preparations or topical preparations containing magnesium. That document neither describes nor suggests the combination of a tablet with a preparation for topical use.

U.S. Pat. No. 5,898,037 recommends treating acne, arthritis, periodontal diseases, ophthalmic diseases such as conjunctivitis, hemorrhoids, and vaginal infections and inflammation with preparations based on magnesium. That patent mentions (i) the administration of a topical preparation containing Mg and (ii), to complement the effect of the first preparation, the administration of an oral preparation also containing Mg (see column 3, lines 11-13 and 30-32, on the one hand, and column 8, lines 58-67, on the other hand). The drawback of the complementary oral preparation lies in the fact that it is required to supply 300 to 900 mg/d of magnesium. This is a massive amount in light of the article by Roth P. et al., 'Intestinal Absorption of Magnesium in Man', International Journal of Applied Radiation and Isotopes, 1979:30, 523-526, which reported on a study of the oral administration of the isotope $^{28}Mg$ to humans and found that the bioavailability, expressed in the form of percentage of magnesium absorbed relative to the weight amount of magnesium administered, decreases when the magnesium dosage increases.

It is likewise known that magnesium, administered topically, also acts on the stress and fatigue of the skin, on the one hand, and the regeneration of the cutaneous barrier, thereby enhancing the moisturizing of the skin, on the other hand.

So it has been noted, on the one hand, that the oral administration of magnesium does not enable a sufficient intake of $Mg^{2+}$ ions in the outermost layers of the epidermis, such as the corneal layer (stratum corneum) and, on the other hand, that the administration of magnesium topically does not enable a sufficient intake of $Mg^{2+}$ ions in the inner layers of the skin, particularly the hypodermis and the inner part of the dermis, when the stratum corneum is deficient in Mg. This is a biological imbalance which the present invention proposes to remedy.

SUMMARY OF THE INVENTION

According to the invention, it is proposed to provide a new technical solution to solve the problem which arises in irrigating $Mg^{2+}$ ions across the thickness of the skin, on the one hand, and to promote the assimilation of the magnesium of topical origin by all of the skin, which is generally stopped by the corneal layer (the desire here, according to the expression of the skilled person, is to "boost" the topical Mg), on the other hand.

In one aspect of the present teachings, this objective can be achieved through the administration of an oral preparation, in tablet form, containing a magnesium source, coupled with the administration of a topical preparation containing magnesium, which results in dual internal/external ('inside/outside') effects of the oral and topical preparations on the skin.

In another aspect of the present teachings, a magnesium-based system is proposed for use in skincare, and preferably comprises:
  (a) a first magnesium source in an oral preparation, in the form of a progressive-release tablet, said source supplying $Mg^{2+}$ ions to the body, the tablet form exhibiting in vitro, after 2 h in 0.1N HCl medium, a rate of dissolution (δ) of the magnesium contained therein of less than or equal to 60% by weight relative to the total weight of the Mg provided by said source, and
  (b) a second magnesium source in a topical preparation, said source supplying $Mg^{2+}$ ions to the skin.

In another aspect of the present teachings, a care kit is proposed that contains said oral preparation and said topical preparation of said system.

In another aspect of the present teachings, a new use of the above-described system is proposed for use in skincare with respect to stress, fatigue, and deficiencies of the cutaneous barrier, particularly with regard to moisturizing.

In short, the systems disclosed above and below may be advantageously used as a cosmetic, e.g., (a) for moisturizing the skin, and (b) for treating or preventing skin stress.

DETAILED DESCRIPTION OF THE INVENTION

A. The Magnesium Sources

The magnesium sources useful according to the invention, which are identical or different, are each a physiologically acceptable magnesium derivative. With regard to the topical preparation, said physiologically acceptable magnesium derivative is selected from the group consisting of
  (α) magnesium oxide, MgO,
  (β) salts of Mg with inorganic acids,
  (γ) salts of Mg with organic acids,
  (δ) hydrates of said inorganic and organic salts, and
  (ε) mixtures thereof.

Inorganic acids which can be used for obtaining the salts (β) include HCl and $H_2SO_4$. The organic acids which can be used for obtaining the salts (γ) notably include:
  simple acids, such as acetic acid, propionic acid, and isobutyric acid (or 2-methyl-2-propionic acid),
  polyacids such as, in particular, oxalic acid, maleic acid, fumaric acid, malonic acid, and citraconic acid (or 2-methyl-2-butenedioic acid),
  hydroxy acids, such as, in particular, malic acid, citric acid, tartaric acid, lactic acid, salicylic acid, vanillic acid, gluconic acid, glucuronic acid, glycerophosphoric acid, mandelic acid, and citramalic acid (or 2-hydroxy-2-methylbutanedioic acid),
  natural or non-natural amino acids, such as, in particular, aspartic acid, glutamic acid, asparagine, lysine, pidolic acid (other names: pyroglutamic acid or 5-oxo-L-proline), pyridine-2-carboxylic acid, pyridine-3-carboxylic acid, pyridine-4-carboxylic acid, aminobutanedioic acid, and orotic acid.

The hydrates (δ) comprise, in particular, the $MgCl_2$ hydrates of formula (I):

$$MgCl_2.n(H_2O) \quad\quad (I)$$

in which n is an integral or fractional number having a value of 1 to 6 (preferably 1 to 9/2).

Suitable mixtures (ε) include marine magnesium. This is a mixture of marine origin which contains at least 70% by weight of inorganic Mg salts. The main production of marine magnesium comes from the exploitation of the Dead Sea.

For topical forms, it is recommended, advantageously, to employ sources (β)-(ε). Generally speaking, for said topical forms, recommendation is given more particularly to $MgCl_2$, the hydrates $MgCl_2.n(H_2O)$ where n is an integral or fractional number having a value of 1 to 9/2, marine magnesium, or a salt of Mg with aspartic acid, glutamic acid, asparagine, lysine, pidolic acid or orotic acid.

With regard to the oral preparation, said physiologically-acceptable magnesium derivative is selected from the group consisting of MgO, $MgCl_2$, and hydrates of formula $MgCl_2.n(H_2O)$ where n is an integral or fractional number greater than 0 and less than or equal to 6. The salts of Mg with the organic acids are generally not suitable here (particularly when they are salts of fatty acids). The reason is that (a) the percentage by weight of the magnesium in these salts goes down when the molecular mass increases, and (b) consequently, these salts result in tablets whose size and mass is too large, and it becomes difficult to swallow them. The reason is that, when the molecular mass of the magnesium source in the tablet increases, the amount of Mg supplied by said source goes down. Whereas the amount of Mg in MgO is 60% by weight, it is 25.5% by weight in $MgCl_2$, and 13.7% by weight in $MgCl_2.9/2(H_2O)$. Consequently, when a tablet is used, it is more advantageous to use an inorganic source of Mg such as $MgCl_2$, $MgCl_2.n(H_2O)$ where n has a value of 1 to 9/2, or marine magnesium, in order to limit the dimensions of said tablet. The preferred source according to the invention is a hydrate, namely $MgCl_2.9/2H_2O$.

B. The Oral Preparations

The oral preparations according to the invention are, as indicated above, progressive-release tablets. Their Mg source provides an amount representing approximately 90 to 110 parts of Mg.

The preparations which are advantageous according to the invention are tablets which exhibit in vitro, after 2 h in 0.1N HCl medium, a rate of dissolution (δ) of the dissolved magnesium of between 20% and 60% by weight relative to the weight of magnesium provided by the magnesium source (i.e., 20%≦δ≦60%), and preferably a rate of dissolution of between 25% and 58% (i.e., 25%≦δ≦58%).

These oral preparations comprise:
  (I) single-layer tablets (referred to as 'single-layer tablets'), containing the entirety of the magnesium source, and
  (II) two-layer tablets (called 'two-layer tablets'), comprising
    (a) a first layer (or 'inner' layer or core) which is enteric, or which is housed in an enteric shell, said first layer containing 80% to 40% of the magnesium provided by the magnesium source, and
    (b) a second layer (or 'outer' layer), which is hydrophilic, which dissolves in the stomach, and which contains 20% to 60% of the magnesium provided by the magnesium source.

C. Particularly Preferred Oral Preparation

In particular, a single-layer oral preparation is preferred which is a progressive-release tablet and which comprises a matrix containing a magnesium source, said matrix being free from an enteric coating, but having a protective coating which slows down or retards the dissolution of Mg in the stomach. An oral preparation of this kind is described in WO 2009/150323.

A particular preferred system comprises, as an oral preparation, a tablet, said tablet taking the form of a coated matrix for oral administration of magnesium with progressive release, said matrix being free from an enteric coating, but having a protective coating that slows down or retards the dissolution of Mg in the system. The preferred matrix includes: said magnesium source (A), a hydrophilic retardant (B1), a hydrophobic retardant (B2), an inert filler (C1) acting as a diluent, and an inert filler (C2) acting as a lubricant. For the administration of (A) 90 to 110 parts by weight of magnesium originating from a source selected from MgO, $MgCl_2$, hydrates of formula $MgCl_2.n(H_2O)$, where n is an integral or fractional number having a value of 1 to 9/2, and mixtures thereof, it preferably further contains the following ingredients:

(B1) 180 to 190 parts by weight of hydroxypropylmethylcellulose, (B2) 19.8 to 22.2 parts by weight of glyceryl behenate, (C1) 10 to 12 parts by weight of lactose, and (C2) 10 to 12 parts by weight of colloidal silica.

Said coating advantageously comprises (D) 15 to 75 parts, and more preferably 15 to 45 parts by weight of a substance selected from shellac, cellulose ethers (especially HPMC and HPC), and mixtures thereof.

In a further preferred aspect of the present teachings, the B1/B2 weight ratio is between 180/22.2=8.1/1 and 190/19.8=9.6/1. Advantageously, it is recommended that said weight ratio is between 8.5/1 and 9.3/1. Preferably, the B1/B2 weight ratio will be between 8.7/1 and 9.2/1, for example, 8.8/1 or 9/1, or else 9.15/1.

The lactose, component C1, is advantageously anhydrous. Similarly, the colloidal silica, component C2, is advantageously anhydrous. In practice, it tends to be preferred for the matrix of the invention to have a C1/C2 weight ratio of close to 1/1 and better still of 1/1.

The coating of the matrix is not enteric. It is a film coating which acts (i) to protect the components of the matrix with respect to the exterior, particularly with respect to impacts, and especially (ii) to slow down the dissolution of Mg in the 'gastric' phase. This film coating may be produced in a single layer, two layers, or even three layers. In order to limit the manufacturing costs, it is possible for it to be a single-layer. Advantageously, however, a two-layer coating is recommended to more effectively control the dissolution of the Mg. The coating of the matrix represents in general 15 to 75 parts by weight (i.e. approximately 1.3% to 7.5% by weight relative to the weight of the matrix), and preferably 15 to 70 parts by weight, and more preferably 15 to 45 parts by weight, per 90 to 110 parts by weight of Mg.

The substances recommended here for the coating are shellac, and film-forming cellulose ethers such as alkylcelluloses, more particularly the mixtures of HPMC and hydroxypropylcellulose (HPC) that are sold, in particular, under the names Nutrateric® and Opadry®. Consideration may also be given to a coating comprised of a first layer of shellac and of an outer layer made from a mixture of alkylcelluloses.

In practice, a coating is recommended which is (a) a single-layer film coating of shellac (used at 50% by weight in ethanol, the solvent being removed during the film coating), or (b) a two-layer film coating, each layer comprising a substance selected from shellac, cellulose ethers (especially HPMC and HPC), and mixtures thereof.

When a two-layer coating is used, the first layer (or inner layer) represents, in general, 0.5% to 4% by weight relative to the weight of the matrix, and the second layer (or outer layer) represents, in general, 0.5% to 3.5% by weight relative to the weight of said matrix, the two said layers together representing 1.3% to 7.5% by weight relative to the weight of said matrix.

The dissolution kinetics of said tablet are determined by means of a dissolution system comprising first the treatment of the tablet constituting the oral preparation in a 0.1N HCl medium [in particular 900 ml, at 40° C. in accordance with the method recommended in the US Pharmacopoeia] from T=0 to T=2 h, then treatment in a buffer [in particular 900 ml, at 40° C.] at pH 6.8 from T=2 h to T=8 h, has a rate of dissolution ($\delta$) of Mg, relative to the Mg administered, such that at T=2 h, $\delta \leq 60\%$, more specifically $20\% \leq \delta \leq 60\%$, and preferably $25\% \leq \delta \leq 58\%$;

at T=4 h, $\delta \leq 85\%$, more specifically $40\% \leq \delta \leq 85\%$, and preferably $45\% \leq \delta \leq 82\%$;

at T=6 h, $\delta \leq 98\%$, more specifically $60\% \leq \delta \leq 98\%$, and preferably $80\% \leq \delta \leq 95\%$; and at T=8 h, $\delta \leq 100\%$, more specifically $90\% \leq \delta \leq 100\%$, and preferably $95\% \leq \delta \leq 99.9\%$.

In this technique for evaluating the dissolution kinetics, the amounts of Mg released are determined by complexometric titration with EDTA. The dissolution kinetics may be determined at a temperature of 15 to 40° C., particularly at ambient temperature (15-25° C.). However, since the components of the oral preparation and the tablets which they constitute are products which do not undergo degradation when stored for a number of months at 40° C., said temperature of 40° C. for assessing said kinetics has been employed in order to be under temperature conditions which are close to those within the human body.

D. The Topical Preparations

The topical preparations which can be used according to the invention include, in particular, creams, gels, lotions, emulsions, aqueous solutions, aqueous-alcoholic solutions, and compositions for atomization. It is possible, for example, to use a topical preparation selected, in particular, from the group consisting of the following:

translucent moisturizing gel,
makeup removing fluid,
relaxing shower gel,
pH-neutral shampoo for frequent use,
soothing emulsion,
soothing cream-gel,
purifying cleansing foam,
regenerating cream, and
anti-aging emulsion.

In practice, the magnesium source of a topical preparation of this kind will advantageously contain an amount of 0.5% to 4% by weight of Mg and preferably 0.8% to 2% by weight of Mg relative to the total weight of said topical preparation.

E. Tests

The system according to the invention is particularly useful as a cosmetic for (i) moisturizing the skin, and/or (ii) treating or preventing skin stress. The cosmetic advantage of the Mg provided by this system to the skin may be assessed by:

measuring the electrical impedance of the skin (expressed in $\Omega$) or its inverse, the conductance (expressed in S), the moisture level in the skin being inversely proportional to the impedance and proportional to the conductance; in this regard, see the methods described by Kalia Y. et al., *Biophys. J.* 1996;71(5):2692-2700, Kalia Y. et al., *J. Pharm. Sci.* 1998;87(12):1508-1811, Curdy C. et al., *AAPS Pharm. Sci.* 2000;2(3):E23, and Clar E. J. et al., *J. Cosm. Chem.* 1975; 26:337-357; and/or analyzing explants of human skin maintained under survival conditions.

F. Dosage

With regard to the dosage, for the aforementioned tablets, it is recommended that a tablet with a 50 or 100 mg dose of magnesium is taken daily (in the morning), or, better still, that two tablets each with a 50 mg dose of magnesium are taken daily (one in the morning, the other in the evening).

For the topical preparations, recommendation is given (i) to application of a gel by massage, once or twice per day, at a rate of 0.2 to 0.8 cm$^3$ of gel for a skin surface area of 2 cm$^2$ per application, or the application of a spray containing 0.8% to 2% by weight of Mg relative to the total weight of said topical preparation, twice per day.

G. Care Kit

In order to satisfy the user and ensure the regularity of the treatment, it is advantageous to present, in a single pack, a care kit, set, case or pouch containing an oral preparation and a topical preparation which are in accordance with the system according to the invention.

H. Conclusions

The system according to the invention acts on the skin and epidermal growths, particularly on the hair, according to a dual aspect. More specifically, it exerts on the skin
(1.) an external action (i) which is beneficial to muscle relaxation and the reinforcement of the cutaneous barrier (this reinforcement being manifested in an increase in moisturizing of the skin), and (ii) which is soothing to the skin; and
(2.) an internal action which is beneficial to muscle relaxation, useful against signs of stress, restorative, anti-inflammatory, and antioxidant (particularly with regard to free radicals of external origin or those generated by the body).

Moreover, according to certain aspects of the present teachings, the system may advantageously produce an equilibrating effect (ionic equilibrium) across the thickness of the skin, internally and externally.

In addition or in the alternative, the oral preparation, which advantageously is in a progressive-release tablet form, preferably "boosts" the topical preparation.

I. EXAMPLES

Other advantages and features of the invention will be appreciated more effectively from reading below of embodiment examples. All these examples are of course not limiting, but are given by way of illustration.

Example 1

(a) Tablets [corresponding to example 5 of the parent application]

Progressive-release single-layer tablets were prepared, each with a dosage of 100 mg of magnesium, and with the formulation below (the B1/B2 weight ratio being 9.15/1), where the abbreviation "Amount/tab" denotes the amount per tablet.

| Constituents | Amount/tab (mg) |
|---|---|
| Core: | |
| MgCl2.9/2H2O | 725.0 |
| HPMC | 183.0 |
| Behenate mono-diglyceride | 20.0 |
| Anhydrous lactose | 11.0 |
| Anhydrous colloidal silica | 11.0 |

-continued

| Constituents | Amount/tab (mg) |
|---|---|
| Film coating: | |
| 1$^{st}$ layer: shellac | 19.8 |
| 2$^{nd}$ layer (outer): 1/4 w/w HPMC/HPC mixture | 19.8 |
| Total: | 989.60 |

(b) Gel

A gel is prepared from an aqueous composition containing hydrophilic colloidal silica and 4% by weight of magnesium pidolate. This gel features the advantage of containing no substances that might interfere in the context of the comparative tests (such as polyols acting as permeation promoters, vitamin E, sunscreen, etc).

(c) Packaging and Dosage

The oral preparation (a) is packaged in the form of a delayed-release tablet, and the topical preparation (b) is packaged in the same kit, the dosage being 1 tablet per day (taken in the morning) and two applications of the gel per day (one in the morning and the other in the evening)

Example 2

The procedure indicated in example 1 above is repeated, with the difference (1.) that in step (a) progressive-release single-layer tablets are prepared each with a dosage of 50 mg of magnesium, and (2.) that in step (c) two of these tablets with a dosage of 50 mg are administered per day (one in the morning, the other in the evening)

Examples 3 and 4

(a) Tablets

The procedure indicated in example 1(a) is repeated for preparing progressive-release single-layer tablets each with a dosage of 100 mg of magnesium, and, respectively, in example 2(a) for preparing progressive-release tablets each with a dosage of 50 mg of magnesium.

(b) Spray

As a topical preparation, a firming spray is employed whose formulation is as follows:

| Component | % (w/w) |
|---|---|
| Propylene glycol | 2.30 |
| Tetrasodium edetate | 0.20 |
| Apple extract | 0.25 |
| Extract of jujube (fruit of the jujube tree) | 0.15 |
| Polyethoxylated jujube extract | 0.20 |
| Polyethoxylated macadamia nut glycerides | 0.08 |
| Palm oil | 0.03 |
| Sodium polyacrylate | 0.02 |
| Vitamin E and preservative | 0.06 |
| Fragrance | 1.00 |
| Magnesium orotate | 1.75 |
| Demineralized water | qs 100 |

(c) Packaging and Dosage

The packaging and dosage are those indicated in examples 1(c) and 2(c) respectively.

Examples 5 and 6

The procedure indicated above in examples 3 and 4, respectively, is repeated using, as the topical composition, a fluid cream whose formulation is as follows:

| Component | % (w/w) |
|---|---|
| Propylene glycol | 2.00 |
| Sodium hyaluronate | 5.00 |
| Cyclomethicone | 5.00 |
| Dimethicone/trisiloxane/ceteth-10/laureth-4 mixture | 3.80 |
| Cyclomethicone/dimethiconol mixture | 3.50 |
| Argan oil | 2.50 |
| 3-Hydroxy-L-proline (20% w/v in $H_2O$) | 2.00 |
| Oat kernel extract | 1.00 |
| Wheat gluten hydrolysate | 1.00 |
| Polysorbate 20 | 1.00 |
| Carbomer (Carbopol Ultrez ® 10) | 0.75 |
| Benzyl acetate | 0.60 |
| Octyl methoxycinnamate | 0.50 |
| Magnesium pidolate | 1.50 |
| Demineralized water | qs 100 |

Examples 7 and 8

The procedure indicated above in examples 3 and 4 is repeated using, as the topical composition, a purifying cleansing ghassoul foam.

Example 9

(a) Tablets [corresponding to example 10 of the parent application]

Progressive-release single-layer tablets were prepared, each with a dosage of 50 mg of magnesium, and having the formulation below (the B 1/B2 weight ratio being 9.15/1).

| Constituents | Amount/tab (mg) |
|---|---|
| Core: | |
| $MgCl_2 \cdot 9/2H_2O$ | 362.50 |
| HPMC | 91.50 |
| Behenate mono-diglyceride | 10.00 |
| Anhydrous lactose | 5.50 |
| Anhydrous colloidal silica | 5.50 |
| Film coating 1: | |
| Shellac (OPAGLOS ® NA715G, product sold by the Colorcon company) | 1.3% to 2.2%* |
| Film coating 2: | |
| 1/3 w/w HPMC/HPC mixture (OPADRY ® VMS, product sold by the Colorcon company) | 1.1% to 1.6%* |
| Yellow 20A38069 | 0.008 |

Note
*percentage by weight relative to the weight of the uncoated tablet.

(b) Gel
The gel of example 1b is employed.
(c) Packaging and Dosage
The oral preparation (a) is packaged in the form of a delayed-release tablet, and the topical preparation (b) is packaged in the same kit, the daily dosage being 2 tablets each containing 50 mg of Mg (one taken in the morning and one taken in the evening), and two applications of the gel per day (one in the morning and the other in the evening)

Example 10

(a) Tablets [corresponding to example 11 of the parent application]

Progressive-release single-layer tablets were prepared (with a dose of 50 mg of magnesium) and had the formulation below (the B1l/B2 weight ratio being 9.15/1).

| Constituents | Amount/tab (mg) |
|---|---|
| Core: | |
| $MgCl_2 \cdot 9/2H_2O$ | 362.50 |
| HPMC | 91.50 |
| Behenate mono-diglyceride | 10.00 |
| Anhydrous lactose | 5.50 |
| Anhydrous colloidal silica | 5.50 |
| Film coating: | |
| Shellac (OPAGLOS ® NA715G, product sold by the Colorcon company) | 1.7%* |

Note
*percentage by weight relative to the weight of the uncoated tablet.

(b) Gel
The gel of example 1b is employed.
(c) Packaging and Dosage
The oral preparation (a) is packaged in the form of a delayed-release tablet, and the topical preparation (b) is packaged in the same kit, the daily dosage being 2 tablets each containing 50 mg of Mg (one taken in the morning and one taken in the evening), and two applications of the gel per day (one in the morning and the other in the evening)

Example 11

(a) Tablets [corresponding to example 12 of the parent application]
Tablets were prepared which had the formulation below (the B1/B2 weight ratio being 9.15/1).

| Constituents | Amount/tab (mg) |
|---|---|
| Core: | |
| $MgCl_2 \cdot 9/2H_2O$ | 362.50 |
| HPMC | 91.50 |
| Behenate mono-diglyceride | 10.00 |
| Anhydrous lactose | 5.50 |
| Anhydrous colloidal silica | 5.50 |
| Film coating 1: | |
| Shellac (OPAGLOS ® NA715G, product sold by the Colorcon company) | 1.7%* |
| Film coating 2: | |
| 1/3 w/w HPMC/HPC mixture (OPADRY VMS, product sold by the Colorcon company) | 0.5%* |

Note
*percentage by weight relative to the weight of the uncoated tablet.

(b) Gel
The gel of example 1b is employed.
(c) Packaging and Dosage
The oral preparation (a) is packaged in the form of a progressive-release tablet, and the topical preparation (b) is packaged in the same kit, the daily dosage being 2 tablets each containing 50 mg of Mg (one taken in the morning and one taken in the evening), and two applications of the gel per day (one in the morning and the other in the evening).

Example 12

(a) Tablets
Progressive-release two-layer tablets were prepared, each with a dosage of 100 mg of magnesium and containing in their inner, enteric layer (the core) 450 mg of $MgCl_2 \cdot 9/2H_2O$ (corresponding to approximately 62 mg of Mg) and in their outer, hydrophilic layer, for release in the stomach, 275 mg of $MgCl_2.9/2H_2O$ (corresponding to approximately 38 mg of Mg). After 2 h in 0.1N HCl, the rate of dissolution δ is of the order of 38%.

(b) Gel

The gel of example 1b is employed.

(c) Packaging and Dosage

The oral preparation (a) is packaged in the form of a progressive-release tablet, and the topical preparation (b) is packaged in the same kit, the daily dosage being 1 tablet containing 100 mg of Mg (one taken in the morning), and two applications of the gel per day (one in the morning and the other in the evening).

The invention claimed is:

1. A magnesium-based system suitable for use in skincare, comprising:
   (a) a first magnesium source in the form of a solid, progressive-release tablet for oral ingestion, said first magnesium source being formulated to supply $Mg^{2+}$ ions to a body, the progressive-release tablet comprising a matrix having a protective coating that slows down or retards the dissolution of Mg in the stomach, said matrix being comprised of said first magnesium source (A), hydroxypropylmethylcellulose (B1), glyceryl behenate (B2), an inert filler (C1) acting as a diluent, and an inert filler (C2) acting as a lubricant, with a weight ratio of B1:B2 being between 8.1:1 and 9.6:1, and exhibiting in vitro, after 2h in 0.1N HCl medium, a rate of dissolution (δ) of the magnesium contained therein of between 20% and 60% by weight relative to the total weight of the Mg provided by said first magnesium source, and
   (b) a second magnesium source in a topical preparation formulated to supply $Mg^{2+}$ ions by application to skin.

2. The system according to claim 1, wherein said progressive-release tablet is selected from the group consisting of:
   (I) a single-layer tablet containing the entirety of the first magnesium source, and
   (II) a two-layer tablet comprising
   (a) a first layer which is enteric, or which is housed in an enteric shell, said first layer containing 80% to 40% of the magnesium provided by the first magnesium source, and
   (b) a second layer, which is hydrophilic, which surrounds said first layer, which dissolves in the stomach, and which contains 20% to 60% of the magnesium provided by the first magnesium source.

3. The system according to claim 1, wherein said matrix forms a core that comprises:
   (A) 90 to 110 parts by weight of magnesium originating from a source selected from MgO, $MgCl_2$, hydrates of the formula $MgCl_2.n(H_2O)$, where n is a whole or fractional number having a value of 1 to 9/2, and mixtures thereof,
   (B1) 180 to 190 parts by weight of hydroxypropylmethylcellulose,
   (B2) 19.8 to 22.2 parts by weight of glyceryl behenate,
   (C1) 10 to 12 parts by weight of lactose, and
   (C2) 10 to 12 parts by weight of colloidal silica.

4. The system according to claim 3, wherein said protective coating comprises
   (D) 15 to 75 parts of a substance selected from shellac, cellulose ethers and mixtures thereof.

5. The system according to claim 1, wherein the second magnesium source is a physiologically-acceptable derivative of magnesium selected from the group consisting of
   (α) magnesium oxide, MgO,
   (β) salts of Mg with inorganic acids,
   (γ) salts of Mg with organic acids,
   (δ) hydrates of said inorganic and organic salts, and
   (ε) mixtures thereof.

6. The system according to claim 1, wherein the first magnesium source is selected from the group consisting of MgO, $MgCl_2$, hydrates $MgCl_2.n(H_2O)$ where n is a whole or fractional number having a value of 1 to 9/2, marine magnesium, and a salt of Mg with at least one of aspartic acid, glutamic acid, asparagine, lysine, pidolic acid and orotic acid.

7. The system according to claim 1, wherein the tablet exhibits a magnesium dissolution rate (δ), as determined by first treating in 900 ml of a 0.1N HCl medium at 40° C. from T=0 to T=2h, and then by treating in 900 ml of a buffer at 40° C. at pH 6.8 from T=2h to T=8h, relative to the total amount of magnesium administered, such that
   at T=4h, δ is less than or equal to 85%;
   at T=6h, δ is less than or equal to 98%; and
   at T=8h, δ is less than or equal to 100%.

8. The system according to claim 7, wherein the magnesium dissolution rate (δ), as determined by the treatment in the HCl medium followed by the buffer, is such that
   at T=2h, δ is between 25-58%;
   at T=4h, δ is between 45-82%;
   at T=6h, δ is between 80-95%; and
   at T=8h, δ is between 95-99.9%.

9. The system according to claim 1, wherein the protective coating comprises an inner layer comprised of shellac and an outer layer comprised of a mixture of alkylcelluloses.

10. The system according to claim 9, wherein the mixture of alkylcelluloses comprises hydroxypropylmethylcellulose and hydroxypropylcellulose.

11. The system according to 1 wherein the topical preparation is selected from the group consisting of cream, gel, lotion, emulsion, aqueous solution, aqueous-alcoholic solution and atomizable composition, and contains 0.5% to 4% by weight of Mg relative to the total weight of the topical preparation.

12. A skin care treatment method comprising:
   orally administering at least once a day, to a patient in need thereof, a first magnesium source in the form of a solid, progressive-release tablet, said first magnesium source being formulated to supply $Mg^{2+}$ ions to the patient's body, the tablet comprising a matrix having a protective coating that slows down or retards the dissolution of Mg in the stomach, said matrix being comprised of said first magnesium source (A), hydroxypropylmethylcellulose (B1), glyceryl behenate (B2), an inert filler (C1) acting as a diluent, and an inert filler (C2) acting as a lubricant, with a weight ratio of B1:B2 being between 8.1:1 and 9.6:1, and exhibiting in vitro, after 2h in 0.1N HCl medium, a rate of dissolution (δ) of the magnesium contained therein of between 20% and 60% by weight relative to the total weight of the Mg provided by the first magnesium source, and
   topically administering at least once a day, to the patient in need thereof, a second magnesium source formulated to supply $Mg^{2+}$ ions to the patient's skin.

13. The method according to claim 12, wherein the tablet exhibits a magnesium dissolution rate (δ), as determined by first treating in 900 ml of a 0.1N HCl medium at 40° C. from T=0 to T=2h, and then by treating in 900 ml of a buffer at 40° C. at pH 6.8 from T=2h to T=8h, relative to the total amount of magnesium administered, such that:
   at T=4h, δ is between 40-85%;
   at T=6h, δ is between 60-98%; and
   at T=8h, δ is between 90-100%.

14. The method according to claim 12, wherein the topical preparation is selected from the group consisting of cream, gel, lotion, emulsion, aqueous solution, aqueous-alcoholic solution and atomizable composition, and contains 0.5% to 4% by weight of Mg relative to the total weight of the topical preparation.

15. The method according to claim 12, wherein said matrix forms a core that comprises:
 (A) 90 to 110 parts by weight of magnesium originating from a first source selected from MgO, $MgCl_2$, hydrates of formula $MgCl_2.n(H_2O)$, where n is an integral or fractional number having a value of 1 to 9/2, and mixtures thereof,
 (B1) 180 to 190 parts by weight of hydroxypropylmethylcellulose,
 (B2) 19.8 to 22.2 parts by weight of glyceryl behenate,
 (C1) 10 to 12 parts by weight of lactose, and
 (C2) 10 to 12 parts by weight of colloidal silica.

16. The method according to claim 15, wherein the first magnesium source in said tablet is $MgCl_2.9/2(H_2O)$.

17. The method according to claim 15, wherein the magnesium dissolution rate ($\delta$) of the tablet, as determined by the treatment in the HCl medium followed by the buffer, is such that:
 at T=2h, $\delta$ is between 25-58%,
 at T=4h, $\delta$ is between 45-82%,
 at T=6h, $\delta$ is between 80-95%,
 at T=8h, $\delta$ is between 95-99.9%,.

18. The method according to claim 12, wherein said protective coating is a single layer coating.

19. The method according to claim 12, wherein said protective coating is a two-layer coating.

20. The method according to claim 12, wherein the protective coating comprises an inner layer comprised of shellac and an outer layer comprised of a mixture of alkylcelluloses.

21. The method according to claim 20, wherein the mixture of alkylcelluloses comprises hydroxypropylmethylcellulose and hydroxypropylcellulose.

* * * * *